United States Patent [19]
Ark

[11] Patent Number: 6,007,540
[45] Date of Patent: Dec. 28, 1999

[54] WAND-STYLE SURGICAL INSTRUMENT WITH LOCKABLE THROTTLE

[75] Inventor: Timmon Ark, Charlottesville, Va.

[73] Assignee: MicroAire Surgical Instruments, Inc., Charlottesville, Va.

[21] Appl. No.: 09/182,422

[22] Filed: Oct. 30, 1998

[51] Int. Cl.⁶ .................................................. A61B 17/00
[52] U.S. Cl. ............................................. 606/80; 606/167
[58] Field of Search ................................ 606/1–9, 80, 82, 606/167, 168, 169, 176

[56] References Cited

U.S. PATENT DOCUMENTS

| | | | |
|---|---|---|---|
| 3,835,860 | 9/1974 | Garreston | 128/310 |
| 4,589,414 | 5/1986 | Yoshida et al. | 128/305 |
| 5,904,687 | 5/1999 | Del Rio et al. | 606/80 |

*Primary Examiner*—Michael Buiz
*Assistant Examiner*—Daphna Shai
*Attorney, Agent, or Firm*—Whitham, Curtis & Whitham

[57] ABSTRACT

A surgical instrument having a locking throttle mechanism. The throttle is pivotally mounted to a wand-type housing by a hinge, and the housing includes a tool tip and a connecting mechanism. The throttle fits in an indented portion of the housing when it is in an ON position. An actuating switch is placed under the throttle and is controlled by a sliding grip/safety switch located on the throttle. A slidable locking mechanism is placed within a cavity of the throttle and may be moved between a locked position and an unlocked position. In the locked position, a portion of the slidable locking mechanism communicates with a locking cavity proximate to the lip of the housing. A spring is located between the throttle and the housing and urges the throttle into an OFF position and is compressed when the throttle is advanced downward towards the housing.

15 Claims, 2 Drawing Sheets

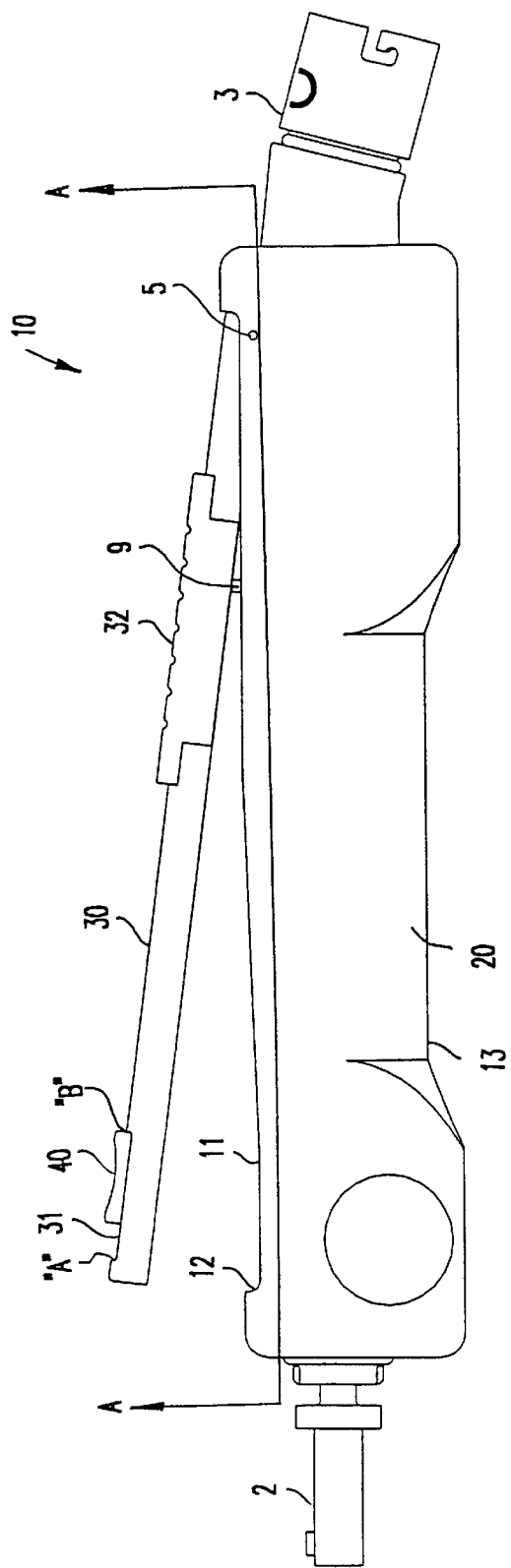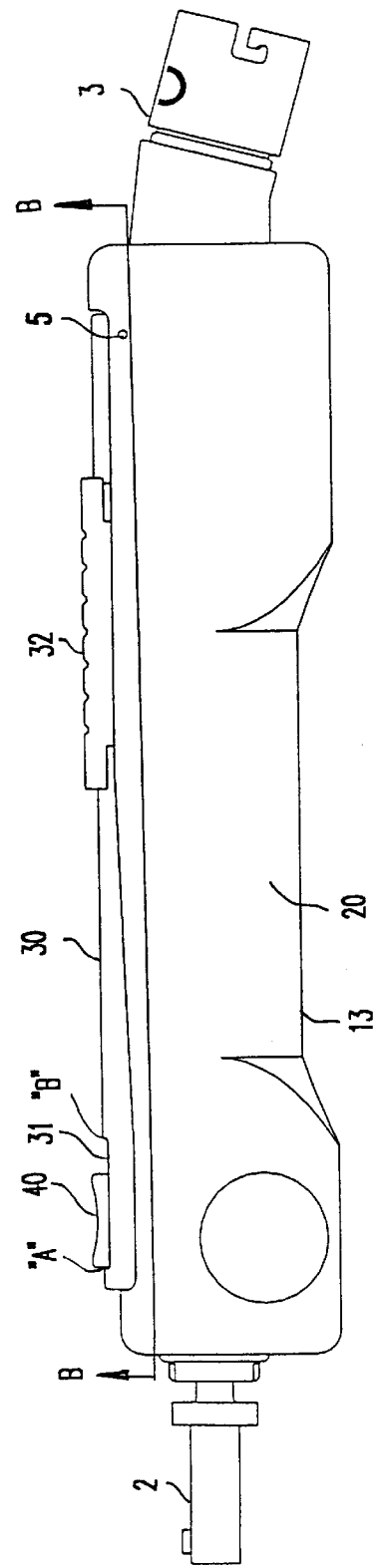

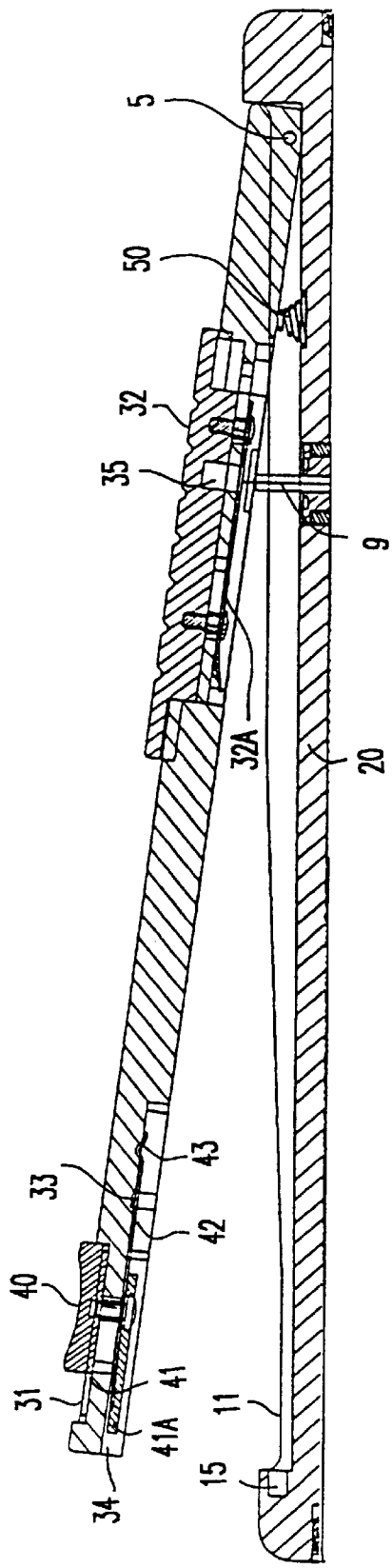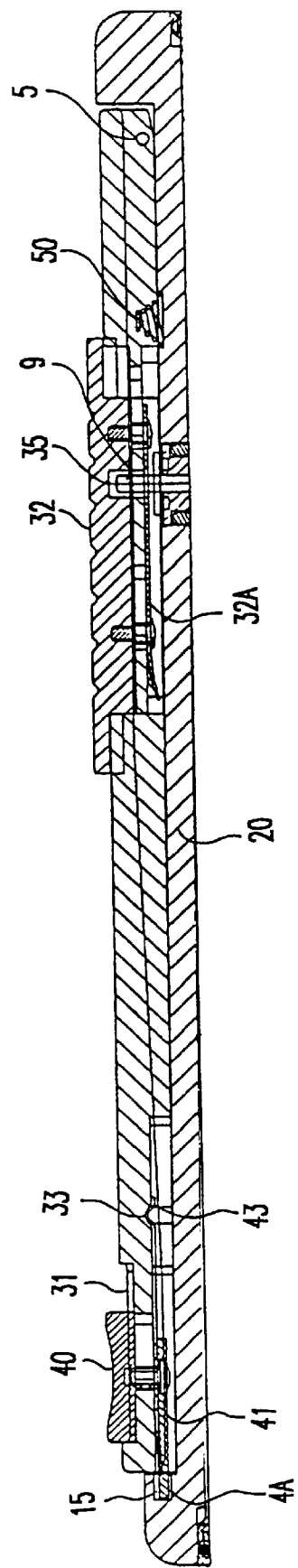

WAND-STYLE SURGICAL INSTRUMENT WITH LOCKABLE THROTTLE

FIELD OF THE INVENTION

The present invention generally relates to a locking throttle and, more particularly, to a wand-style surgical instrument having a locking throttle mechanism.

BACKGROUND DESCRIPTION

There are countless medical devices that are currently being used by medical professionals, such as surgeons, dentists, etc. These medical devices include, amongst others, saws, drills, screw drivers and other tools (collectively referred to as "surgical instruments"). These surgical instruments typically operate using electrical or pneumatic motors which are activated by a trigger or throttle mechanism.

In order to use these surgical instruments, a medical professional must activate the motor by actuating the trigger or throttle or other activating mechanism. The activation of the trigger or throttle is performed by placing pressure on the activating mechanism such that when a maximum amount of pressure is placed on the activating mechanism, the electrical or pneumatic motor is "running" at full speed. Thus, for the surgical instrument to properly operate during a medical procedure the medical professional must constantly place pressure on the activating mechanism, such as the trigger, which depending on the surgical procedure, may last for an extended period of time (e.g., minutes to hours).

Placing constant pressure on the activating mechanism of the surgical instrument poses several problems for the medical professional, not the least of which is fatigue to the medical professional's hand. Of course, present activating mechanisms also pose other problems which need to be addressed by designers of surgical tools. Specifically, it may be difficult for the medical professional at times to both manipulate the surgical instrument and simultaneously apply pressure to the activating mechanism during use thereof. This not only poses a problem to the medical professional, but it also may pose a danger to the patient. For example, when using a wand-style surgical instrument, the medical professional may have to position the surgical instrument in such a position that constant pressure cannot be applied to the activating mechanism at a critical time during the medical procedure, thus leading to unacceptable results.

What is needed is a locking system that is easy to use and provides safeguards for both the medical professional using the medical device and the patient. Such a system would provide safety features so that the locking mechanism cannot be accidently deactivated by the medical professional. This locking mechanism would also provide a safety switch so that when the trigger is inadvertently activated, the driving motor will not engage therein.

SUMMARY OF THE INVENTION

The present invention is directed to a surgical instrument having a locking throttle mechanism. In particular, a throttle is pivotally mounted to a wand-type housing by a hinge. A tool tip and a connecting mechanism are provided at opposing ends of the surgical instrument.

The housing can be substantially cylindrical in shape and may include an indented portion having a lip near the end of the tool tip. In various embodiment, discussed in detail below embodiments, the throttle fits in the indented portion when it is in a partially ON position or a fully "ON" position when used with surgical tools having variable speed motors, and forms an integral part of the housing. The housing may also include a contoured portion in order to accommodate a user's hand. An actuating switch is placed under the throttle and is controlled by a sliding grip/safety switch located on the throttle.

A slidable locking mechanism is placed within a cavity of the throttle and is movable between a locked position and an unlocked position. In the locked position, a portion of the slidable locking mechanism communicates with a locking cavity proximate to the lip of the housing. A spring is located between the throttle and the housing and urges the throttle into an "OFF" position and is compressed when the throttle is advanced downward towards the housing (i.e., to the ON position).

BRIEF DESCRIPTION OF THE DRAWINGS

The foregoing and other objects, aspects and advantages will be better understood from the following detailed description of a preferred embodiment of the invention with reference to the drawings, in which:

FIG. 1 is a side view of a surgical instrument with a throttle in the OFF position;

FIG. 2 is a side view of a surgical instrument with a throttle in the ON position;

FIG. 3 is an view exploded of FIG. 1 along the line A—A; and

FIG. 4 is an view exploded of FIG. 2 along the line B—B.

DETAILED DESCRIPTION OF A PREFERRED EMBODIMENT OF THE INVENTION

The present invention is directed to a surgical instrument having a locking throttle mechanism. In a preferred embodiment, the surgical instrument having a locking throttle mechanism is used in medical devices, such as, reciprocating liposuction handpiece or drill systems; however, other systems, such as, for example, screw drivers, saws and other tools, are equally contemplated for use with the present invention. Thus, the present invention is not limited to reciprocating liposuction handpiece or drill systems, but is equally applicable to other medical and non-medical tools. It is also noted that the surgical instrument of the present invention may utilize an electric motor or be equally powered by a pneumatic mechanism or other well known driving mechanism, all of which are not critical to the understanding of the present invention.

By using the locking throttle mechanism of the present invention, a user may operate the surgical tool without applying pressure to an activating mechanism, such as a throttle mechanism, during use thereof. This allows the user to better manipulate the surgical instrument without the added concern of whether the surgical instrument will operate in its intended manner (e.g., whether the motor is activated). Also, the surgical instrument of the present invention includes a safety mechanism so that when the locking mechanism is locked when the throttle is in the ON position, a safety switch must still be activated in order to operate the surgical instrument of the present invention.

Referring now to FIG. 1, a side view of the surgical instrument 10 having a locking throttle mechanism in an OFF position is shown. In particular, a throttle 30 is pivotally mounted to a wand-type housing 20. The throttle 30 may be mounted to the housing 20, for example, by a hinge 5. A tool tip 2 is provided at a distal end of the surgical instrument 10 and a connecting mechanism 3 is provided at a proximal end of the surgical instrument 10. The tool tip 2 may accommodate several different types of tools, such as liposuction cannulas, drills, saws and the like, and the connecting mechanism 3 may accommodate an electrical or pneumatic connection system. It is understood that both the tool tip 2 and connecting mechanism 3 are not critical to the understanding of the present invention and a detailed discussion of the tool tip 2 and connecting mechanism 3 is thus omitted herein.

As further seen in FIG. 1, the housing 20 is substantially cylindrical in shape (although other shapes are equally contemplated for use with the present invention, such as, for example, rectangular or square shapes) and may include an indented portion 11 having a lip 12 at the distal end of the surgical tool 10, proximate the tool tip 2. The housing 20 may also include a contoured portion 13 on an underside of the housing 20 so as to accommodate a user's hand. The throttle 30 fits in the indented portion 11 when in a fully ON position (e.g., when the throttle 30 rests on the housing 20) (FIG. 2) such that, in embodiments, the throttle 30 forms an integral part of the housing 20. In further embodiments, the throttle 30 rests on an upper surface of the housing 20 when in the ON position. In variable speed motors, the throttle 30 need not be fully depressed in order to activate the motor. An actuating switch 9 is placed under the throttle 30 and is controlled by a sliding grip/safety switch 32 located on the throttle 30, and will be discussed with respect to FIG. 4.

Referring still to FIG. 1, a sidable locking mechanism 40 is placed within a cavity 31 of the throttle 30; however, the slidable locking mechanism 40 may merely be positioned on an upper surface of the throttle 30, and not in a cavity. The sidable locking mechanism 40 is movable between a locked position "A" and an unlocked position "B". In the locked position "A", a portion of the slidable locking mechanism 40 communicates with a locking cavity proximate to the lip 12 of the housing 20 (FIG. 4).

FIG. 2 shows a side view of the surgical instrument 10 with the throttle 30 in the ON position. In this position, the actuating lever 40 is in the locked position "A". Also, the sliding grip/safety switch 32 is in the closed position such that the actuating switch 9 is in a non-activated position.

FIG. 3 shows an exploded view of FIG. 1 along the line A—A. Specifically, FIG. 3 shows a spring 50 placed between the throttle 30 and surface of the housing 20. The spring 50 urges the throttle 30 into the OFF position (e.g., when the throttle 30 is fully extended upward with respect to the housing 20) and is compressed when the throttle 30 is advanced downward towards the housing 20 in the ON position. It is further noted that the spring 50 may be located at various positions along the housing 20, and other urging mechanisms may be used by the present invention, such as, for example, a spring loaded lever or a resilient material.

As further seen in FIG. 3, the slidable locking mechanism 40 includes a leaf spring 42 and a sliding lock portion 41 on the underside of the throttle 30. In embodiments, the leaf spring 42 and the sliding lock portion 41 oppose one another and are further provided in a cutout 34 on the underside of the throttle 30; however the leaf spring 42 and the sliding lock portion 41 may be placed on the underside of the throttle and not in a cutout. The leaf spring 42 includes a step portion 43 which bears against an upper surface of the cutout 34. A locking cavity 15 located on the lip 12 of the housing 20 and a notch 33 is provided on the underside of the throttle, preferably within the cutout 34. In a locked position, an end portion 41A of the sliding lock portion 41 communicates with the locking cavity 15 in order to lock the throttle 30 in the locked position "A", and the step portion 43 communicates with the notch 33 in order to maintain the slidable locking mechanism 40 in the locked position "A".

FIG. 4 shows an exploded view of FIG. 2 along the line B—B, and more specifically, the sliding lock portion 41 communicating with the locking cavity 15. As further seen in FIG. 4, when the throttle 30 is in the ON position, the spring 50 is compressed between the throttle 30 and the housing 20. As clearly seen in FIG. 4, when the locking mechanism 40 slides into the locked position "A", the end portion 41A of the sliding lock portion 41 communicates with the locking cavity 15 in order to lock the throttle 30 in an ON position.

In preferred embodiments, when the sliding grip/safety switch 32 is in a first position (e.g., closed position) (shown), the actuating switch 9 communicates with a bore 35 of the sliding grip/safety switch 32 so that a driving motor of the surgical instrument is not activated when the throttle 30 is in the ON position. However, when the sliding grip/safety switch 32 is in an opposing second position (e.g., opened position) (not shown), the actuating switch 9 communicates with a bottom surface 32A of the sliding grip/safety switch 32 such that the driving motor of the surgical instrument is activated when the throttle 30 is in the ON position. The driving motor of the surgical instrument will not be activated when the throttle 30 is in the OFF position, but can be regulated as the throttle is advanced downward toward the housing 20, as seen in FIGS. 1 and 3.

While the invention has been described in terms of a single preferred embodiment, those skilled in the art will recognize that the invention can be practiced with modification within the spirit and scope of the appended claims.

Having thus described our invention, what we claim as new and desire to secure by Letters Patent is as follows:

1. A surgical tool having a locking mechanism comprising:

a housing including an indented portion, said indented portion having a lip at a first end;

a locking cavity located within the lip of the indented portion;

a throttle mechanism pivotally mounted to the housing at a first end;

a locking mechanism slidable on the throttle mechanism at a second end opposing the first end, the locking mechanism communicating with the locking cavity when the throttle is in an ON position in order to lock the throttle in the ON position.

2. The surgical tool of claim 1, wherein the throttle forms an integral portion of the housing when the throttle is in the ON position.

3. The surgical tool of claim 1, wherein the throttle further comprises:

a cavity on an upperside of the throttle proximate to the second end; and a cutout on an underside of the throttle proximate to the second end and substantially opposing the cavity.

4. The surgical tool of claim 3, wherein the locking mechanism comprises:

a sliding grip located in the cavity of the throttle; and a sliding lock portion located in the cutout of the throttle, an end portion of the sliding lock portion communicating with the locking cavity when the sliding grip is moved into a first position and the throttle is in the ON position.

5. The surgical tool of claim 4, wherein:

the locking mechanism further comprises a leaf spring opposing the sliding lock portion, the leaf spring has a step portion bearing against an underside surface of the throttle in the cutout; and the throttle further comprises a notch in the underside surface of the throttle in the cutout, the step portion of the leaf spring rests in the notch when the sliding grip is moved into the first position and the throttle is in the ON position.

6. The surgical tool of claim 1, further comprising a sliding grip/safety switch located on the throttle, the sliding grip/safety switch having a first position and a second position, and a bore on an underside of the sliding grip/safety switch, when the sliding grip/safety switch 32 is in the first position an actuating switch extending from the housing communicates with the bore so that a driving motor of the surgical tool is not activated when the throttle is in an ON position.

7. The surgical tool of claim 1, further comprising a spring located substantially between the housing and the throttle, the spring urging the throttle in an OFF position and the spring being compressed when the throttle is an ON position.

8. The surgical tool of claim 1, wherein the surgical instrument is a reciprocating liposuction device.

9. A surgical tool having a locking mechanism comprising:

a housing having a lip at a first end;

a locking cavity located within the lip;

a throttle mechanism pivotally mounted to the housing at a first end;

a locking mechanism sidable on the throttle mechanism;

wherein the locking mechanism communicates with the locking cavity in order to lock the throttle in an ON position.

10. The surgical tool of claim 9, wherein housing includes an indented portion such that the throttle forms an integral portion of the housing when the throttle is in an ON position.

11. The surgical tool of claim 9, wherein the throttle further comprises:

a cavity on an upperside of the throttle; and a cutout on an underside of the throttle and substantially opposing the cavity.

12. The surgical tool of claim 11, wherein the locking mechanism comprises:

a sliding grip located in the cavity of the throttle; and a sliding lock portion located in the cutout of the throttle, an end portion of the sliding lock portion communicating with the locking cavity when the sliding grip is moved into a first position and the throttle is in the ON position.

13. The surgical tool of claim 12, wherein:

the locking mechanism further comprises a leaf spring, the leaf spring has a step portion bearing against an underside surface of the throttle in the cutout; and the throttle further comprises a notch in the underside surface of the throttle in the cutout, the step portion of the leaf spring rests in the notch when the sliding grip is moved into the first position and the throttle is in the ON position.

14. A surgical tool having a locking mechanism comprising:

a housing having a lip at a first end;

a locking cavity located within the lip;

a throttle mechanism pivotally mounted to the housing at a first end;

a locking mechanism slidable on the throttle mechanism, the locking mechanism including a sliding grip located on an upperside of the throttle and a sliding lock portion located on the underside of the throttle, an end portion of the sliding lock portion communicating with the locking cavity when the sliding grip is moved into a first position and the throttle is in an ON position.

15. The surgical tool of claim 14, wherein the throttle further comprises:

a cavity on an upperside of the throttle; and a cutout on an underside of the throttle and substantially opposing the cavity, wherein the sliding grip is located in the cavity and the sliding lock portion is located in the cutout.

\* \* \* \* \*